United States Patent
Miyake et al.

(10) Patent No.: US 11,780,791 B2
(45) Date of Patent: Oct. 10, 2023

(54) (6Z,9Z)-6,9-DODECADIEN-1-YNE AND A PROCESS FOR PREPARING THE SAME

(71) Applicant: Shin-Etsu Chemical Co., Ltd., Tokyo (JP)

(72) Inventors: Yuki Miyake, Joetsu (JP); Takeshi Kinsho, Joetsu (JP); Ryo Komatsu, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 17/718,376

(22) Filed: Apr. 12, 2022

(65) Prior Publication Data

US 2022/0332667 A1 Oct. 20, 2022

(30) Foreign Application Priority Data

Apr. 14, 2021 (JP) ................................. 2021-068439

(51) Int. Cl.
| | | |
|---|---|---|
| C07C 11/28 | (2006.01) | |
| C07C 33/02 | (2006.01) | |
| C07C 2/86 | (2006.01) | |
| C07C 29/44 | (2006.01) | |
| C07C 33/048 | (2006.01) | |
| C07C 67/40 | (2006.01) | |
| C07C 29/17 | (2006.01) | |

(52) U.S. Cl.
CPC ............... *C07C 11/28* (2013.01); *C07C 2/861* (2013.01); *C07C 29/17* (2013.01); *C07C 29/44* (2013.01); *C07C 33/02* (2013.01); *C07C 33/048* (2013.01); *C07C 67/40* (2013.01)

(58) Field of Classification Search
CPC ......... C07C 2/861; C07C 29/44; C07C 29/17; C07C 33/02
See application file for complete search history.

(56) References Cited

U.S. PATENT DOCUMENTS 5,728,376 A * 3/1998 Attygalle .............. C07C 33/048
568/903
9,181,164 B1 * 11/2015 Bercot ..................... C07C 47/21

FOREIGN PATENT DOCUMENTS

| CN | 104844452 B | 12/2019 |
| EP | 2639217 A1 | 9/2013 |
| WO | 9633612 A1 | 10/1996 |

OTHER PUBLICATIONS

Attygalle et al. "(3E,87,11Z)-3,8,11-Tetradecatrienyl Acetate, Major Sex Pheromone Component of the Tomato Pest *Scrobipalpuloides absoluta* (Lepidoptera: Gelechiidae)" Bioorganic & Medicinal Chemistry, 4(3):305-314 (1996).

Cabezas, Jorge A. "A new and efficient synthesis of (3E,8Z, 1 lZ)-tetradeca-3,8, 11-trienyl acetate, the major sex pheromone component of the tomato leafminer Tuta absoluta" Tetrahedron Letters, 60:407-410 (2019).

Extended European Search Report corresponding to European Patent Application No. 22167780.0 (9 pages) (dated Sep. 22, 2022).

Attygalle et al. "Microscale, random reduction: Application to the characterization of (3E,8Z,11Z)-3,8,11-tetradecatrienyl acetate, a new lepidopteran sex pheromone" Tetrahedron Letters, 36(31):5471-5474 (1995).

Puigmarti et al. "An Improved and Convenient New Synthesis of the Pheromone Components of the Tomato Leafminer Tuta absoluta" Synthesis, 47:961-968 (2015).

Svatos et al. "Sex pheromone of tomato pest *Scrobipalpuloides absoluta* (Lepidoptera: Gelechiidae)" Journal of Chemical Ecology, 22:787-800 (1996).

Witzgall et al. "Sex Pheromones and Their Impact on Pest Management" Journal of Chemical Ecology, 36:80-100 (2010).

* cited by examiner

*Primary Examiner* — Yate' K Cutliff
(74) *Attorney, Agent, or Firm* — Myers Bigel, P.A.

(57) ABSTRACT

The present invention provides (6Z,9Z)-6,9-dodecadien-1-yne of the following formula (1). Further, the present invention provides a process for preparing (6Z,9Z)-6,9-dodecadien-1-yne (1): the process comprising reacting a (3Z,6Z)-10-halo-3,6-decadiene compound of the following general formula (2), wherein X represents a halogen atom with a metal acetylide of the following general formula (3), wherein M represents Na, Li, K, Ag, Cu (I), MgZ, CaZ, or Cu(II)Z, wherein Z represents a halogen atom or an ethinyl group to form (6Z,9Z)-6,9-dodecadien-1-yne (1).

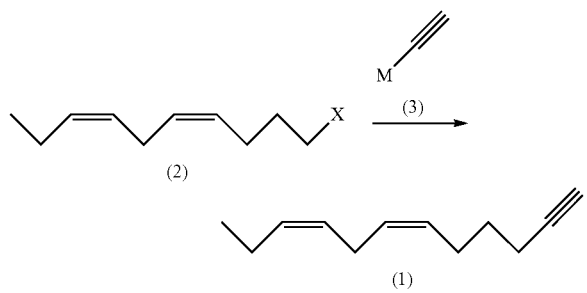

5 Claims, No Drawings

(6Z,9Z)-6,9-DODECADIEN-1-YNE AND A PROCESS FOR PREPARING THE SAME

TECHNICAL FIELD

The present invention relates to (6Z,9Z)-6,9-dodecadien-1-yne and a process for preparing the same.

BACKGROUND ART

Tomato leafminer (*Tuta absoluta*), which is one of the most serious pests against tomato originated in South America, invaded Spain in 2006 and has spread rapidly to Europe such as Spain, Italy, and France; Africa such as Morocco, Tunisia, and Nigeria; Middle East such as Turkey, Israel, and Iran; and Asia such as India, Nepal, China, Taiwan and Japan. Twenty % of tomatoes is estimated to be lost by this pest throughout the world. Thus, controlling this pest is extremely important to prevent the serious damage. Depending on temperatures of its habitats, tomato leafminer has such a short life cycle as 10 or more generations per year and, therefore, easily develops resistance to insecticides. Accordingly, insecticides often lose their effectiveness for this pest in several years after start of the application, so that it is very difficult to control this pest with insecticides. Accordingly, biological control methods to which pests cannot easily develop resistance have been attracting attention. As one of them, a mating disruption method utilizing sex pheromones has been increasingly used to control this species throughout the world.

The sex pheromone composition of *Tuta absoluta* is reported to be a 90:10 mixture of (3E,8Z,11Z)-3,8,11-tetradecatrienyl acetate and (3E,8Z)-3,8-tetradecadienyl acetate (Non-Patent Literature 1 listed below).

However, a process for industrially preparing the main component, (3E,8Z,11Z)-3,8,11-tetradecatrienyl acetate, has not been established, which prevents extensive use of a mating disruption method for controlling *Tuta absoluta* (Non-Patent Literature 2 listed below).

A process for preparing (3E,8Z,11Z)-3,8,11-tetradecatrienyl acetate is described in Non-Patent Literature 3 listed below. In the process, 2-(3-butyn-1-yloxy)tetrahydro-2H-pyran is reacted with n-butyllithium in THF, followed by a coupling reaction with (3Z,6Z)-10-bromo-3,6-decadiene in a mixed solvent of THF and N,N'-dimethylpropylene urea (DMPU) to form tetrahydro-2-[(8Z,11Z)-8,11-tetradecadien-3-yn-1-yloxy]-2H-pyran. Next, the tetrahydropyranyl (THP) group of the obtained tetrahydro-2-[(8Z,11Z)-8,11-tetradecadien-3-yn-1-yloxy]-2H-pyran thus prepared is removed in the presence of Dowex (trademark) 50W-X8 in methanol to form (8Z,11Z)-8,11-tetradecadien-3-yn-1-ol. Subsequently, (8Z,11Z)-8,11-tetradecadien-3-yn-1-ol thus prepared is reduced with lithium aluminum hydride to form (3E,8Z,11Z)-3,8,11-tetradecatrien-1-ol, and the hydroxyl group of (3E,8Z,11Z)-3,8,11-tetradecatrien-1-ol thus prepared is acetylated with acetic anhydride.

Another process for preparing (3E,8Z,11Z)-3,8,11-tetradecatrienyl acetate is described in Non-Patent Literature 4 listed below. In the process, 2-(3-butyn-1-yloxy)tetrahydro-2H-pyran is reacted with n-butyllithium in THF, and followed by a coupling reaction with (3Z,6Z)-10-bromo-3,6-decadiene in a mixed solvent of THF and hexamethylphosphoric triamide (HMPA) to form tetrahydro-2-[(8Z,11Z)-8,11-tetradecadien-3-yn-1-yloxy]-2H-pyran. Next, tetrahydro-2-[(8Z,11Z)-8,11-tetradecadien-3-yn-1-yloxy]-2H-pyran thus prepared is subjected to Birch reduction to form tetrahydro-2-[(3E,8Z,11Z)-3,8,11-tetradecatrienyloxy]-2H-pyran. Subsequently, the tetrahydropyranyl (THP) group of the obtained tetrahydro-2-[(3E,8Z,11Z)-3,8,11-tetradecatrienyloxy]-2H-pyran thus prepared is removed in the presence of an acid catalyst in methanol to form (3E,8Z,11Z)-3,8,11-tetradecatrien-1-ol. The hydroxyl group of (3E,8Z,11Z)-3,8,11-tetradecatrien-1-ol thus prepared is then acetylated with acetic anhydride.

LIST OF THE LITERATURES

Non-Patent Literatures

[Non-Patent Literature 1] Athula B. Attygalle et al., 1996, J. Chem. Ecol., 22(4): 787-800.
[Non-Patent Literature 2] Peter Witzgall et al., 2010, J. Chem. Ecol., 36(1): 80-100.
[Non-Patent Literature 3] Athula B. Attygalle et al., 1995, Tetrahedron Letters., 36(31): 5471-5474.
[Non-Patent Literature 4] Angel Guerrero et al., 2015, Synthesis, 47(07): 961-968.

Problems to be Solved by the Invention

However, in both of the preparation processes described in Non-Patent Literatures 3 and 4, 2-(3-butyn-1-yloxy)tetrahydro-2H-pyran, which is very expensive, is used as a starting material. Although 2-(3-butyn-1-yloxy)tetrahydro-2H-pyran can be prepared by reacting 3-butyn-1-ol with dihydropyran (DHP) in the presence of an acid catalyst, both of 3-butyn-1-ol and DHP are difficult to commercially purchase in low prices. Therefore, these preparation processes are unsuitable for industrial production. As mentioned in Non-Patent Literature 1, in the coupling reaction of 2-(3-butyn-1-yloxy)tetrahydro-2H-pyran, it is most likely that 2-hydroxytetrahydropyran is eliminated to leave (8Z, 11Z)-1,8,11-tetradecatrien-3-yne as a byproduct, which is undesirable in view of the purity. Besides, expensive Dowex (trademark) is used in the preparation process described in Non-Patent Literature 3, so that this process is economically disadvantageous. In the preparation process described in Non-Patent Literature 4, the carcinogenic hexamethylphosphoric triamide and n-butyllithium, which is difficult to handle because of its sensitivity to air or water and its ignitability on exposure to air, are used in large amounts as solvents. Accordingly, the process is difficult to carry out in an industrial scale. As stated above, both of the preparation processes described in Non-Patent Literatures 3 and 4 have the problems in industrial production of (8Z,11Z)-8,11-tetradecadien-3-yn-1-ol which is an intermediate for preparing (3E,8Z,11Z)-3,8,11-tetradecatrienyl acetate which is a sex pheromone component of *Tuta absoluta*.

SUMMARY OF THE INVENTION

The present invention has been made in these circumstances, and aims to provide a compound that is a precursor for industrially preparing (8Z,11Z)-8,11-tetradecadien-3-yn-1-ol. The present invention also aims to provide a process for preparing the compound.

As a result of the intensive researches to overcome the aforesaid problems of the prior art, the present inventors have successfully prepared (6Z,9Z)-6,9-dodecadien-1-yne and have found that this compound is a useful intermediate for preparing (8Z,11Z)-8,11-tetradecadien-3-yn-1-ol. The present inventors also have found that (3E,8Z,11Z)-3,8,11-tetradecatrienyl acetate, which is a sex pheromone component of *Tuta absoluta*, may be prepared from (6Z,9Z)-6,9- dodecadien-1-yne, using inexpensive starting materials in less steps, and thus have completed the present invention.

According to one aspect of the present invention, the present invention provides (6Z,9Z)-6,9-dodecadien-1-yne of the following formula (1):

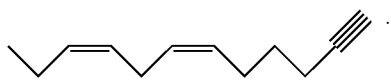
(1)

According to another aspect of the present invention, the present invention provides a process for preparing (6Z,9Z)-6,9-dodecadien-1-yne of the following formula (1):

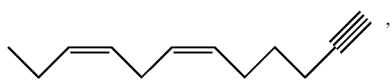
(1)

the process comprising:
reacting a (3Z,6Z)-10-halo-3,6-decadiene compound of the following general formula (2):

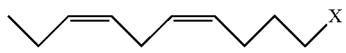
(2)

wherein X represents a halogen atom
with a metal acetylide of the following general formula (3):

  MC≡CH (3)

wherein M represents Na, Li, K, Ag, Cu (I), MgZ, CaZ, or Cu(II)Z, wherein Z represents a halogen atom or an ethinyl group
to form (6Z,9Z)-6,9-dodecadien-1-yne (1).

According to another aspect of the present invention, the present invention provides a process for preparing (8Z,11Z)-8,11-tetradecadien-3-yn-1-ol of the following formula (4):

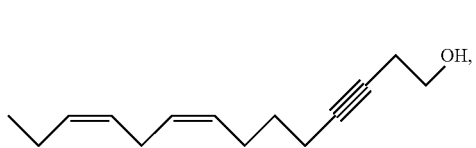
(4)

the process comprising:
reacting (6Z,9Z)-6,9-dodecadien-1-yne (1) with a base; and
subjecting a reaction mixture thus obtained to a homologation reaction with ethylene oxide to form (8Z,11Z)-8,11-tetradecadien-3-yn-1-ol (4).

According to another aspect of the present invention, the present invention provides a process for preparing (3E,8Z,11Z)-3,8,11-tetradecatrien-1-ol of the following formula (5):

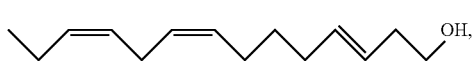
(5)

the process comprising:
the aforesaid process for preparing (8Z,11Z)-8,11-tetradecadien-3-yn-1-ol (4); and
subjecting (8Z,11Z)-8,11-tetradecadien-3-yn-1-ol (4) to a reduction reaction to form (3E,8Z,11Z)-3,8,11-tetradecatrien-1-ol (5).

According to another aspect of the present invention, the present invention provides a process for preparing (3E,8Z,11Z)-3,8,11-tetradecatrienyl acetate of the following formula (6):

(6)

wherein Ac represents an acetyl group,
the process comprising:
the aforesaid process for preparing (3E,8Z,11Z)-3,8,11-tetradecatrien-1-ol (5); and
acetylating (3E,8Z,11Z)-3,8,11-tetradecatrien-1-ol (5) to form (3E,8Z,11Z)-3,8,11-tetradecatrienyl acetate (6).

According to the present invention, it is possible to industrially prepare (8Z,11Z)-8,11-tetradecadien-3-yn-1-ol (4) and (3E,8Z,11Z)-3,8,11-tetradecatrienyl acetate (6) in less steps without expensive starting materials. According to the present invention, it is also possible to provide useful synthetic intermediates for preparing the two compounds.

DETAILED DESCRIPTION OF THE PREFERRED EMBODIMENTS

A. (6Z,9Z)-6,9-dodecadien-1-yne (1)

Preparation of (6Z,9Z)-6,9-dodecadien-1-yne (1)

(6Z,9Z)-6,9-Dodecadien-1-yne of the following formula (1) may be prepared by reacting a (3Z,6Z)-10-halo-3,6-decadiene compound of the following general formula (2) with a metal acetylide of the following general formula (3). This reaction is a nucleophilic substitution reaction between the (3Z,6Z)-10-halo-3,6-decadiene compound (2) and the metal acetylide (3).

wherein X represents a halogen atom, and M represents a metal.

(3Z,6Z)-10-Halo-3,6-decadiene Compound (2)

First, a (3Z,6Z)-10-halo-3,6-decadiene compound of the following general formula (2) will be described.

X represents a halogen atom. The halogen atom X is specifically a chlorine atom, a bromine atom, or an iodine atom and is preferably a bromine atom or an iodine atom in view of the reactivity.

Specific examples of the (3Z,6Z)-10-halo-3,6-decadiene compound (2) include the following compounds: (3Z,6Z)-10-chloro-3,6-decadiene, (3Z,6Z)-10-bromo-3,6-decadiene, and (3Z,6Z)-10-iodo-3,6-decadiene.

The (3Z,6Z)-10-halo-3,6-decadiene compound (2) may be used either alone or in combination thereof, if necessary.

The (3Z,6Z)-10-halo-3,6-decadiene compound (2) may be commercially available one or may be prepared in house, for example, by halogenating (4Z,7Z)-4,7-decadien-1-ol.

Metal Acetylide (3)

Next, a metal acetylide of the following general formula (3) will be described.

MC≡CH    (3)

M represents Na, Li, K, Ag, Cu(I), MgZ, CaZ, or Cu(II)Z, wherein Z represents a halogen atom or an ethinyl group. Examples of the halogen atom include a chlorine atom, a bromine atom, and an iodine atom. The halogen atom is preferably a bromine atom or an iodine atom in view of the reactivity.

M is preferably Na, Li, Cu(I), or Cu(II)Z in view of the reactivity.

Specific examples of the metal acetylide (3) include the following compounds: sodium acetylide, lithium acetylide, potassium acetylide, magnesium acetylide, calcium acetylide, copper acetylide, and silver acetylide. The metal acetylide compound (3) is preferably sodium acetylide, lithium acetylide, or copper acetylide in view of the reactivity.

The metal acetylide (3) may be prepared in house, for example, by reacting heated sodium or magnesium with acetylene or reacting n-butyllithium with acetylene.

Nucleophilic Substitution Reaction

The metal acetylide (3) may be used either alone or in combination thereof, if necessary. The metal acetylide compound (3) may be commercially available one.

An amount of the metal acetylide (3) used is preferably from 1.0 to 10.0 mol, more preferably from 1.0 to 3.0 mol, per mol of the (3Z,6Z)-10-halo-3,6-decadiene compound (2) in view of the reactivity.

A solvent may be incorporated in the nucleophilic substitution reaction, if necessary.

Examples of the solvent include common solvents, for example, ethers such as diethyl ether, dibutyl ether, 4-methyltetrahydropyran, tetrahydrofuran (THF), 2-methyltetrahydrofuran (2-MeTHF), cyclopentyl methyl ether, and 1,4-dioxane;

hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone (GBL), N-methylpyrrolidone (NMP), N,N-dimethylformamide (DMF), N,N-dimethylacetamide (DMAC), and hexamethylphosphoric triamide (HMPA); nitriles such as acetonitrile and propionitrile; and esters such as methyl acetate, ethyl acetate, n-propyl acetate, and n-butyl acetate. The solvent is preferably an ether such as 4-methyltetrahydropyran, tetrahydrofuran, or 2-methyltetrahydrofuran (2-MeTHF); a hydrocarbon such as toluene or xylene; or an aprotic polar solvent such as N,N-dimethylformamide or N,N-dimethylacetamide, and is more preferably a hydrocarbon or an aprotic polar solvent, in view of the reactivity.

The solvent may be used either alone or in combination thereof, if necessary. The solvent may be commercially available one.

An amount of the solvent used in the nucleophilic substitution reaction is preferably from 0 to 7000 g, more preferably from 0 to 3000 g, per mol of the (3Z,6Z)-10-halo-3,6-decadiene compound (2).

A reaction temperature in the nucleophilic substitution reaction varies, depending on the metal acetylide (3) and/or the solvent to be used, and is preferably from −20 to 180° C., more preferably from 0 to 100° C. in view of the reactivity.

A reaction time of the nucleophilic substitution reaction varies, depending on the metal acetylide (3), the solvent to be used, and/or a production scale, and is preferably from 0.5 to 100 hours in view of the reactivity.

Thus, (6Z,9Z)-6,9-dodecadien-1-yne (1) may be prepared from the (3Z,6Z)-10-halo-3,6-decadiene compound (2) and the metal acetylide (3) prepared from acetylene and a metal, such as sodium, which are inexpensive industrial starting materials.

B. Preparation of (8Z,11Z)-8,11-tetradecadien-3-yn-1-ol (4)

(8Z,11Z)-8,11-Tetradecadien-3-yn-1-ol of the following formula (4) may be prepared by reacting (6Z,9Z)-6,9-dodecadien-1-yne (1) with a base, followed by a homologation reaction with ethylene oxide.

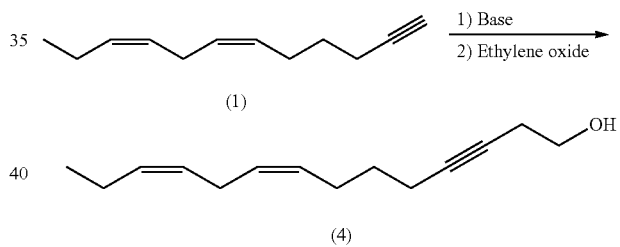

Examples of the base incorporated in the homologation reaction include organolithium reagents such as n-butyllithium, tert-butyllithium, methyllithium, and phenyllithium; Grignard reagents such as methylmagnesium chloride, methylmagnesium bromide, methylmagnesium iodide, ethylmagnesium chloride, n-propylmagnesium chloride, n-butylmagnesium chloride, isopropylmagnesium chloride, and phenylmagnesium chloride; metal acetylides such as sodium acetylide, lithium acetylide, potassium acetylide, magnesium acetylide, calcium acetylide, copper acetylide, silver acetylide, and aluminum acetylide; and metal hydride reagents such as sodium hydride and potassium hydride. The base is preferably an organolithium reagent, a Grignard reagent, or a metal acetylide in view of the safety and is more preferably a Grignard reagent in view of the availability.

An amount of the base used is preferably from 1.0 to 10.0 mol, more preferably from 1.0 to 3.0 mol, per mol of (6Z,9Z)-6,9-dodecadien-1-yne (1) in view of the reactivity.

An amount of ethylene oxide used is preferably from 1.0 to 10.0 mol, more preferably from 1.0 to 5.0 mol, per mol of (6Z,9Z)-6,9-dodecadien-1-yne (1) in view of the reactivity.

A solvent may be used in the homologation reaction, if necessary. Examples of the solvent include common solvents, for example, ethers such as diethyl ether, dibutyl ether, 4-methyltetrahydropyran, tetrahydrofuran (THF), 2-methyltetrahydrofuran (2-MeTHF), cyclopentyl methyl ether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone (GBL), N-methylpyrrolidone (NMP), N,N-dimethylformamide (DMF), N,N-dimethylacetamide (DMAC), and hexamethylphosphoric triamide (HMPA); and nitriles such as acetonitrile and propionitrile. The solvent is preferably an ether such as diethyl ether, tetrahydrofuran, 2-methyltetrahydrofuran, or 4-methyltetrahydropyran; or a hydrocarbon such as toluene or xylene in view of the reactivity.

The solvent may be used either alone or in combination thereof, if necessary. The solvent may be commercially available one.

An amount of the solvent used is preferably from 20 to 7000 g, more preferably from 50 to 3000 g, per mol of (6Z,9Z)-6,9-dodecadien-1-yne (1) in view of the reactivity.

A reaction temperature in the homologation reaction varies, depending on the base and/or the solvent to be used, and is preferably from −40 to 180° C., more preferably from −10 to 100° C., in view of the reactivity.

A reaction time of the homologation reaction varies, depending on the base, the solvent to be used, and/or a production scale, and is preferably from 0.5 to 100 hours in view of the reactivity.

Thus, (8Z,11Z)-8,11-tetradecadien-3-yn-1-ol (4), which is an important intermediate for the preparation of a sex pheromone of *Tuta absoluta*, may be prepared from (6Z,9Z)-6,9-dodecadien-1-yne (1), inexpensive base and ethylene oxide, as raw materials.

C. Preparation of (3E,8Z,11Z)-3,8,11-tetradecatrien-1-ol (5)

(3E,8Z,11Z)-3,8,11-Tetradecatrien-1-ol of the following formula (5) may be prepared by subjecting (8Z,11Z)-8,11-tetradecadien-3-yn-1-ol (4) to a reduction reaction. The reduction reaction causes conversion of the carbon-carbon triple bond in (8Z,11Z)-8,11-tetradecadien-3-yn-1-ol (4) to a double bond.

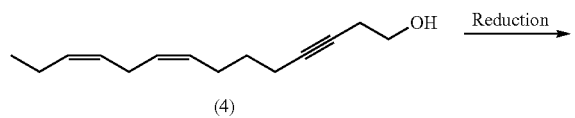

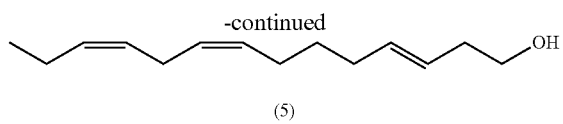

(5)

Examples of the reduction reaction to prepare (3E,8Z,11Z)-3,8,11-tetradecatrien-1-ol (5) include (i) reduction with an organoaluminium compound, (ii) Birch reduction, (iii) ammonia-free Birch reduction, and (iv) Benkeser reduction.

(i) Reduction with an Organoaluminium Compound

The reduction with an organoaluminium compound includes hydroalumination with an organoaluminium compound in a solvent, followed by hydrolysis.

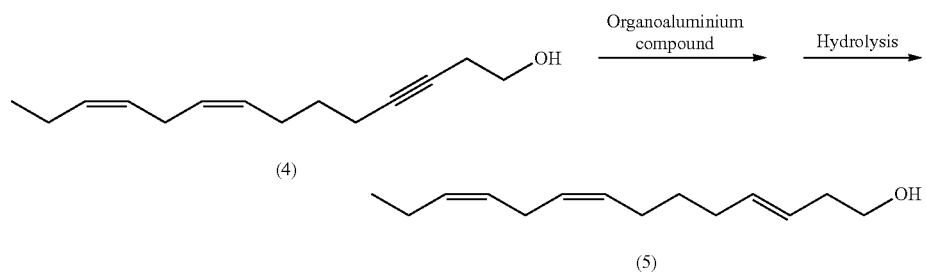

Examples of the organoaluminium compound used in the hydroalumination include lithium aluminum hydride, sodium bis(2-methoxyethoxy)aluminum hydride (Red-Al), and diisobutylaluminum hydride (DIBAL).

An amount of the organoaluminium compound used in the hydroalumination is preferably from 0.25 to 100 mol, more preferably from 0.50 to 20 mol, per mol of (8Z,11Z)-8,11-tetradecadien-3-yn-1-ol (4) in view of the reactivity.

Examples of the solvent used in the hydroalumination include ethers such as diethyl ether, dibutyl ether, 4-methyltetrahydropyran, tetrahydrofuran (THF), 2-methyltetrahydrofuran (2-MeTHF), cyclopentyl methyl ether, 1,4-dioxane, and diethylene glycol dimethyl ether; and hydrocarbons such as hexane, heptane, benzene, toluene, xylene, and cumene. The solvent is preferably an ether such as tetrahydrofuran, 2-methyltetrahydrofuran, 4-methyltetrahydropyran, or diethylene glycol dimethyl ether; or a hydrocarbon such as hexane or toluene in view of the reactivity.

The solvent may be used either alone or in combination thereof, if necessary. The solvent may be commercially available one.

An amount of the solvent used is preferably from 20 to 20000 g, more preferably from 50 to 9000 g, per mol of (8Z,11Z)-8,11-tetradecadien-3-yn-1-ol (4) in view of the reactivity.

A reaction temperature in the hydroalumination varies, depending on the organoaluminium compound and/or the solvent to be used, and is preferably from 0 to 250° C., more preferably from 60 to 150° C., in view of the reactivity.

A reaction time of the hydroalumination varies, depending on the organoaluminium compound, the solvent to be used, and/or a production scale, and is preferably from 0.1 to 100 hours, more preferably from 0.1 to 5 hours, in view of the reactivity.

After the hydroalumination, hydrolysis is carried out with an acid or a base in a solvent.

Examples of the acid used in the hydrolysis after the hydroalumination include carboxylic acids such as acetic acid, propionic acid, butyric acid, pentanoic acid, pivalic acid, heptanoic acid, trifluoroacetic acid, chloroacetic acid, formic acid, and oxalic acid; sulfonic acids such as p-toluenesulfonic acid; and mineral acids such as sulfuric acid, hydrochloric acid, nitric acid, and phosphoric acid. The acid is preferably a carboxylic acid such as acetic acid or a mineral acid such as hydrochloric acid in view of the reactivity.

An amount of the acid used is preferably from 0.00010 to 100.0 mol, per mol of (8Z,11Z)-8,11-tetradecadien-3-yn-1-ol (4) in view of the reactivity.

Examples of the base used in the hydrolysis after the hydroalumination include sodium hydroxide, potassium hydroxide, and calcium hydroxide.

An amount of the base used is preferably from 0.00010 to 100.0 mol, per mol of (8Z,11Z)-8,11-tetradecadien-3-yn-1-ol (4) in view of the reactivity.

A solvent and its amount used in the hydrolysis may be same as in the hydroalumination because the hydrolysis is carried out in the reaction system of the hydroalumination.

A reaction temperature in the hydrolysis varies, depending on the reagent to be used, and is preferably from 0° C. to 80° C. in view of the reaction rate.

A reaction time of the hydrolysis varies, depending on a reaction temperature and/or a reaction scale, and is preferably from 0.5 to 100 hours in view of the reactivity.

(ii) Birch Reduction

The Birch reduction is carried out using a metal in ammonia.

[Chemical scheme showing compound (4) converted to compound (5) with Metal/NH$_3$]

An amount of ammonia used is preferably from 1.0 to 10000 mol, more preferably from 10 to 3000 mol, per mol of (8Z,11Z)-8,11-tetradecadien-3-yn-1-ol (4) in view of the reactivity.

Examples of the metal include alkaline metals such as potassium, sodium, and lithium; and alkaline earth metals such as calcium and magnesium.

The metal may be used either alone or in combination thereof, if necessary.

An amount of the metal used is preferably from 1.0 to 1000 mol, more preferably from 1.0 to 100 mol, per mol of (8Z,11Z)-8,11-tetradecadien-3-yn-1-ol (4) in view of the reactivity.

In the Birch reduction, a proton source is preferably incorporated in addition to ammonia. Examples of the proton source include alcohols such as methanol, ethanol, n-propanol, 2-propanol, and 2-methyl-2-propanol; and tetrahydrofuran (THF) and, 2-methyltetrahydrofuran (2-MeTHF).

The proton source may be used either alone or in combination thereof, if necessary. The proton source may be commercially available one.

An amount of the proton source used is preferably from 1.0 to 10000 mol, more preferably from 1.0 to 3000 mol, per mol of (8Z,11Z)-8,11-tetradecadien-3-yn-1-ol (4) in view of the reactivity.

A reaction temperature in the Birch reduction is preferably from −78 to 0° C., more preferably from −78 to −33° C., in view of the reactivity.

A reaction time of the Birch reduction varies, depending on a production scale, and is preferably from 0.5 to 100 hours in view of the reactivity.

(iii) Ammonia-Free Birch Reduction

The ammonia-free Birch reduction is carried out using a metal in a crown ether.

[Chemical scheme showing compound (4) converted to compound (5) with Metal/Crown ether]

Examples of the crown ether include 12-crown-4, 15-crown-5, 18-crown-6, dibenzo-18-crown-6, and diaza-18-crown-6.

The crown ether may be used either alone or in combination thereof, if necessary. The crown ether may be commercially available one.

An amount of the crown ether used is preferably from 1.0 to 100.0 mol, more preferably from 1.0 to 20.0 mol, per mol of (8Z,11Z)-8,11-tetradecadien-3-yn-1-ol (4) in view of the reactivity.

Examples of the metal include alkaline metals such as potassium, sodium, and lithium; and alkaline earth metals such as calcium and magnesium.

The metal may be used either alone or in combination thereof, if necessary.

An amount of the metal used is preferably from 1.0 to 100.0 mol, more preferably from 1.0 to 20.0 mol, per mol of (8Z,11Z)-8,11-tetradecadien-3-yn-1-ol (4) in view of the reactivity.

In the ammonia-free Birch reduction, a proton source is preferably incorporated in addition to the crown ether. Examples of the proton source include alcohols such as methanol, ethanol, n-propanol, 2-propanol, and 2-methyl-2-propanol; and tetrahydrofuran (THF) and 2-methyltetrahydrofuran (2-MeTHF).

The proton source may be used either alone or in combination thereof, if necessary. The proton source may be commercially available one.

An amount of the proton source used is preferably from 1.0 to 100.0 mol, more preferably from 1.0 to 20.0 mol, per mol of (8Z,11Z)-8,11-tetradecadien-3-yn-1-ol (4) in view of the reactivity.

A reaction temperature in the ammonia-free Birch reduction varies, depending on the metal and/or the crown ether to be used, and is preferably from −78 to 100° C., more preferably from −40 to 40° C. in view of the reactivity.

A reaction time of the ammonia-free Birch reduction varies, depending on the metal and/or the crown ether to be used and/or a production scale, and is preferably from 0.1 to 100 hours, more preferably from 0.1 to 5 hours in view of the reactivity.

(iv) Benkeser Reduction

The Benkeser reduction is carried out using a metal in an alkylamine.

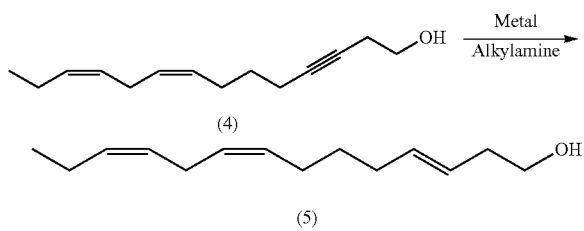

Examples of the alkylamine include lower amines such as methylamine, ethylamine, propylamine, and 1,3-propanediamine.

An amount of the alkylamine used is preferably from 1.0 to 5000 mol, more preferably from 1.0 to 1000 mol, per mol of (8Z,11Z)-8,11-tetradecadien-3-yn-1-ol (4) in view of the reactivity.

Examples of the metal include alkaline metals such as potassium, sodium, and lithium; and alkaline earth metals such as calcium and magnesium.

The metal may be used either alone or in combination thereof, if necessary.

An amount of the metal used is preferably from 1.0 to 1000 mol, more preferably from 1.0 to 100 mol, per mol of (8Z,11Z)-8,11-tetradecadien-3-yn-1-ol (4) in view of the reactivity.

A reaction temperature in the Benkeser reduction is preferably from −78 to 100° C., more preferably from −78 to 60° C. in view of the reactivity.

A reaction time of the Benkeser reduction varies, depending on a production scale, and is preferably from 0.5 to 100 hours in view of the reactivity.

D. Preparation of (3E,8Z,11Z)-3,8,11-tetradecatrienyl acetate (6)

(3E,8Z,11Z)-3,8,11-Tetradecatrienyl acetate of the following formula (6) may be prepared by acetylating (3E,8Z,11Z)-3,8,11-tetradecatrien-1-ol (5).

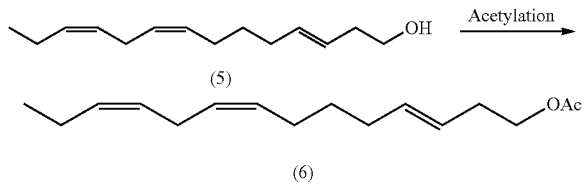

The acetylation may be carried out using an acetylating agent.

Examples of the acetylating agent include acid anhydrides such as acetic anhydride; acetyl halide compounds such as acetyl chloride, acetyl bromide, and acetyl iodide; and acetate ester compounds such as methyl acetate and ethyl acetate. The acetylating agent is preferably acetic anhydride or an acetyl halide compound in view of availability.

An amount of the acetylating agent used is preferably from 1.0 to 10.0 mol, more preferably from 1.0 to 5.0 mol, per mol of (3E,8Z,11Z)-3,8,11-tetradecatrien-1-ol (5) in view of the reactivity and economy.

An acid or a base may be incorporated in the acetylation, if necessary.

Examples of the acid include mineral acids such as hydrochloric acid, sulfuric acid, and nitric acid; aromatic sulfonic acids such as benzenesulfonic acid and p-toluenesulfonic acid; and Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, magnesium chloride, magnesium bromide, titanium tetrachloride, titanium tetrabromide, titanium (IV) methoxide, titanium (IV) ethoxide, titanium (IV) isopropoxide, and titanium (IV) oxide.

The acid may be used either alone or in combination thereof, if necessary.

An amount of the acid used is preferably from 0.001 to 3.00 mol, more preferably from 0.01 to 1.50 mol, per mol of (3E,8Z,11Z)-3,8,11-tetradecatrien-1-ol (5) in view of the reactivity and economy.

Example of the base include trialkylamine compounds such as trimethylamine, triethylamine, and N,N-diisopropylethylamine; cyclic amine compounds such as piperidine, pyrrolidine, and 1,8-diazabicyclo[5.4.0]-7-undecene (DBU); aromatic amine compounds such as pyridine, lutidine, N,N-dimethylaniline, N,N-diethylaniline, N,N-dibutylaniline, and 4-dimethylaminopyridine; and metal alkoxides such as sodium methoxide, sodium ethoxide, sodium t-butoxide, sodium t-amiloxide, lithium methoxide, lithium ethoxide, lithium t-butoxide, lithium t-amiloxide, potassium methoxide, potassium ethoxide, potassium t-butoxide, and potassium t-amiloxide.

The base may be used either alone or in combination thereof, if necessary.

An amount of the base used is preferably from 0.010 to 10.0 mol, more preferably from 1.0 to 5.0 mol, per mol of (3E,8Z,11Z)-3,8,11-tetradecatrien-1-ol (5) in view of the reactivity and economy.

A solvent may be incorporated in the acetylation, if necessary.

Examples of the solvent include common solvents, for example, ethers such as diethyl ether, dibutyl ether, 4-methyltetrahydropyran, tetrahydrofuran (THF), 2-methyltetrahydrofuran (2-MeTHF), cyclopentyl methyl ether, and 1,4-dioxane; hydrocarbons such as hexane, heptane, benzene, toluene, xylene, and cumene; chlorinated solvents such as trichloroethylene, dichloromethane, and chloroform; aprotic polar solvents such as dimethyl sulfoxide, γ-butyrolactone (GBL), N-methylpyrrolidone (NMP), N,N-dimethylformamide (DMF), N,N-dimethylacetamide (DMAC), and hexamethylphosphoric triamide (HMPA); nitriles such as acetonitrile and propionitrile; and esters such as methyl acetate, ethyl acetate, n-propyl acetate, and n-butyl acetate.

The solvent is preferably a hydrocarbon such as toluene or xylene in view of the reactivity.

The solvent may be used either alone or in combination thereof, if necessary. The solvent may be commercially available one.

The acetylation may be carried out in a solvent, if necessary, or without a solvent.

An amount of the solvent used in the acetylation is preferably from 0 to 5000 g, more preferably from 0 to 2000 g, per mol of (3E,8Z,11Z)-3,8,11-tetradecatrien-1-ol (5).

Thus, (3E,8Z,11Z)-3,8,11-tetradecatrienyl acetate (6) may be efficiently prepared from the intermediate, (6Z,9Z)-6,9-dodecadien-1-yne (1), in less steps.

EXAMPLES

The present invention will be explained with reference to the following Examples. It should be noted that the present invention is not limited to or by the Examples.

The term "purity" as used herein means an area percentage in gas chromatography (GC), unless otherwise specified. The term "production ratio" means a ratio of area percentages in GC. The term "yield" is calculated from the area percentages determined by GC.

In the Examples, monitoring of the reactions and calculation of the yields were carried out in the following GC conditions.

GC conditions: GC: Capillary gas chromatograph GC-2014 (Shimadzu Corporation); column: DB-WAX, 0.25 µm×0.25 mmϕ×30 m, carrier gas: He (1.55 mL/min), detector: FID, column temperature: 150° C., elevated by 5° C./min, up to 230° C.

The yield was calculated according to the following equation in consideration of purities (% GC) of a starting material and a product.

Yield (%)={[(mass of a product obtained in a reaction×% GC)/molecular mass of a product]÷[(mass of a starting material×% GC)/molecular mass of a starting material]}× 100

THF represents tetrahydrofuran, and DMF represents N,N-dimethylformamide.

Example 1: Preparation of (6Z,9Z)-6,9-dodecadien-1-yne (1)

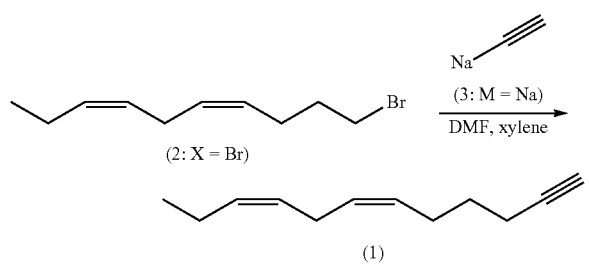

A solution (125.09 g) of sodium acetylide (3: M=Na) (0.60 mol) in xylene and DMF (122.80 g) were placed in a reactor at room temperature and stirred at 38 to 42° C. for 32 minutes. After the completion of the stirring, (3Z,6Z)-10-bromo-3,6-decadiene (2: X=Br) (119.18 g, 0.46 mol, purity 83.48%) was added dropwise at 38 to 42° C. After the completion of the dropwise addition, the mixture was stirred at 38 to 42° C. for 17 hours. Subsequently, water (137.31 g) was added to the reaction mixture, and the reaction mixture was phase-separated. The aqueous phase was removed to obtain the organic phase. The resulting organic phase was concentrated at a reduced pressure. The concentrate was subjected to distillation at a reduced pressure to obtain (6Z,9Z)-6,9-dodecadien-1-yne (1) (71.15 g, 0.35 mol, purity 80.53%, b.p.=95.2 to 99.0° C./1.87 kPa (14.0 mmHg)) in a yield of 77.05%.

The following are spectrum data of (6Z,9Z)-6,9-dodecadien-1-yne (1) thus prepared.

Nuclear magnetic resonance spectrum: $^1$H-NMR (500 MHz, CDCl$_3$): δ=0.97 (3H, t, J=7.7 Hz), 1.60 (2H, dt, J=7.3 Hz, 7.3 Hz), 1.95 (1H, t, J=2.7 Hz), 2.08 (2H, quin-like, J=7.3 Hz), 2.16-2.23 (4H, m), 2.80 (2H, dd, J=6.9 Hz, 6.9 Hz), 5.27-5.45 (4H, m); $^{13}$C-NMR (500 MHz, CDCl$_3$): δ=14.27, 17.84, 20.52, 25.51, 26.10, 28.34, 68.32, 84.35, 127.15, 128.61, 129.22, 131.88.

Mass spectrum: EI-mass spectrum (70 eV): m/z 161 (M$^+$−1), 147, 133, 119, 105, 91, 79, 67, 55, 41.

Infrared absorption spectrum (D-ATR): ν=3309, 3010, 2963, 2934, 1456, 1274, 718, 632.

Example 2: Preparation of (8Z,11Z)-8,11-tetradecadien-3-yn-1-ol (4)

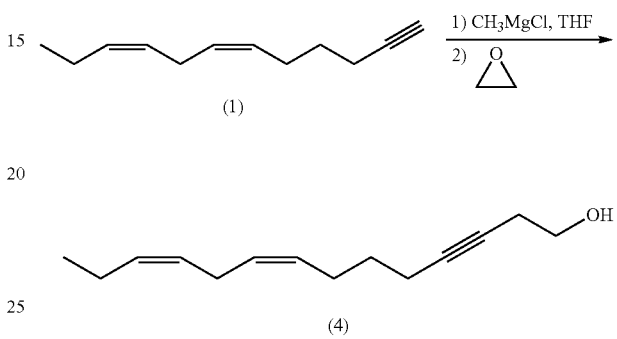

A solution (58.79 g) of methylmagnesium chloride (0.15 mol) in THF was placed in a reactor at room temperature, and (6Z,9Z)-6,9-dodecadien-1-yne (1) obtained in Example 1 (22.51 g, 0.11 mol, purity 80.53%) was added dropwise at 25 to 60° C. After the completion of the dropwise addition, the mixture was stirred at 60 to 65° C. for 3.5 hours. Subsequently, ethylene oxide (7.56 g, 0.17 mol) was added dropwise at 50 to 60° C. After the completion of the dropwise addition, the mixture was stirred at 50 to 60° C. for 3 hours. After the conversion was confirmed to be 100% by GC, an aqueous solution of acetic acid (acetic acid (23.48 g) and water (44.03 g)) was added to the reaction mixture. The reaction mixture was phase-separated, followed by removal of the aqueous phase to obtain the organic phase. The resulting organic phase was concentrated at a reduced pressure. The concentrate was subjected to distillation at a reduced pressure to obtain (8Z,11Z)-8,11-tetradecadien-3-yn-1-ol (4) (26.52 g, 0.11 mol, purity 84.01%, b.p.=111.7 to 120.2° C./0.40 kPa (3.0 mmHg)) in a yield of 96.66%.

The following are spectrum data of (8Z,11Z)-8,11-tetradecadien-3-yn-1-ol (4) thus prepared.

Nuclear magnetic resonance spectrum: $^1$H-NMR (500 MHz, CDCl$_3$): δ=0.97 (3H, t, J=7.3 Hz), 1.55 (2H, dt, J=7.3 Hz, 7.3 Hz), 1.89 (1H, br. s), 2.07 (2H, quin-like, J=7.5 Hz), 2.15 (2H, t, J=6.5 Hz), 2.17 (2H, ddt, J=2.3 Hz, 2.3 Hz, 7.3 Hz), 2.42 (2H, ddt, J=2.3 Hz, 2.3 Hz, 6.5 Hz), 2.78 (2H, dd, J=6.5 Hz, 6.5 Hz), 3.67 (2H, t, J=6.5 Hz), 5.26-5.41 (4H, m); $^{13}$C-NMR (500 MHz, CDCl$_3$): δ=14.24, 18.19, 20.50, 23.13, 25.48, 26.24, 28.79, 61.33, 76.55, 82.31, 127.17, 128.80, 129.02, 131.87.

Mass spectrum: EI-mass spectrum (70 eV): m/z 205 (M$^+$−1), 175, 159, 145, 119, 105, 91, 67, 41.

Infrared absorption spectrum (D-ATR): ν=3336, 2962, 2933, 1455, 1434, 1337, 1045, 849, 718.

Example 3: Preparation of (3E,8Z,11Z)-3,8,11-tetradecatrien-1-ol (5)

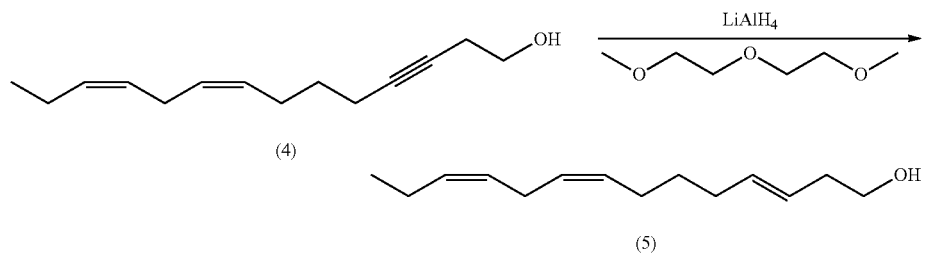

Lithium aluminum hydride (7.73 g, 0.20 mol) and diethylene glycol dimethyl ether (210.83 g) were placed in a reactor at room temperature and stirred at 15 to 20° C. for 24 hours. Subsequently, (8Z,11Z)-8,11-tetradecadien-3-yn-1-ol (4) obtained in Example 2 (15.02 g, 0.061 mol, purity 84.01%) was added dropwise at 25 to 50° C. After the completion of the dropwise addition, the mixture was stirred at 120 to 125° C. for 3 hours and then cooled to 50° C. THF (532.23 g), water (34.05 g), an aqueous solution (4.65 g) of sodium hydroxide (0.029 mol), and celite (96.31 g) were added, and the mixture was filtrated, followed by phase separation and removal of the aqueous phase to obtain the organic phase. The resulting organic phase was concentrated at a reduced pressure. The concentrate was subjected to distillation at a reduced pressure to obtain (3E,8Z,11Z)-3,8,11-tetradecatrien-1-ol (5) (10.70 g, 0.37 mol, purity 72.01%, b.p.=111.7 to 114.1° C./0.40 kPa (3.0 mmHg)) in a yield of 60.49%.

The following are spectrum data of (3E,8Z,11Z)-3,8,11-tetradecatrien-1-ol (5) thus prepared.

Nuclear magnetic resonance spectrum: $^1$H-NMR (500 MHz, CDCl$_3$): δ=0.97 (3H, t, J=7.7 Hz), 1.43 (2H, tt, J=7.3 Hz, 7.3 Hz), 1.54 (1H, t-like, J=5.4 Hz), 1.98-2.11 (6H, m), 2.26 (2H, q-like, J=6.7 Hz), 2.76 (2H, t-like, J=6.5 Hz), 3.61 (2H, q-like, J=6.1 Hz), 5.29 (1H, dtt, J=10.7 Hz, 7.3 Hz, 1.6 Hz), 5.32-5.43 (4H, m), 5.55 (1H, dtt, J=15.3 Hz, 6.9 Hz, 1.2 Hz); $^{13}$C-NMR (500 MHz, CDCl$_3$): δ=14.25, 20.50, 25.48, 26.63, 29.33, 32.18, 35.95, 61.99, 126.06, 127.25, 128.32, 129.63, 131.78, 133.82.

Mass spectrum: EI-mass spectrum (70 eV): m/z 208 (M$^+$), 190, 163, 149, 135, 121, 107, 93, 79, 67, 55, 41.

Infrared absorption spectrum (D-ATR): ν=3336, 2962, 2929, 1455, 1398, 1048, 968, 914, 718.

Example 4: Preparation of (3E,8Z,11Z)-3,8,11-tetradecatrienyl acetate (6)

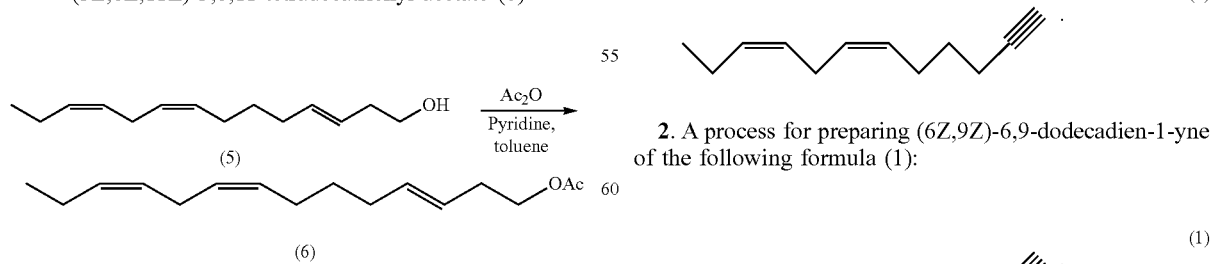

(3E,8Z,11Z)-3,8,11-Tetradecatrien-1-ol (5) (119.16 g, 0.46 mol, purity 80.08%), pyridine (39.85 g, 0.50 mol), and toluene (120.00 g) were placed in a reactor at room temperature and stirred at 15 to 25° C. for 10 minutes. After the completion of the stirring, acetic anhydride (Ac$_2$O) (65.71 g, 0.64 mol) was added dropwise at 20 to 40° C., and the mixture was stirred at 30 to 35° C. for 2 hours. Next, water (138.54 g) was added to the reaction mixture, followed by phase separation and removal of the aqueous phase to obtain the organic phase. The resulting organic phase was washed with an aqueous solution of sodium bicarbonate (sodium bicarbonate (5.22 g) and water (104.15 g)). The organic phase was concentrated at a reduced pressure. The concentrate was subjected to distillation at a reduced pressure to obtain (3E,8Z,11Z)-3,8,11-tetradecatrienyl acetate (6) (125.85 g, 0.44 mol, purity 86.60, b.p.=134.0 to 141.1° C./0.40 kPa (3.0 mmHg)) in a yield of 95.04%.

The following are spectrum data of (3E,8Z,11Z)-3,8,11-tetradecatrienyl acetate (6) thus prepared.

Nuclear magnetic resonance spectrum: $^1$H-NMR (500 MHz, CDCl$_3$): δ=0.97 (3H, t, J=7.3 Hz), 1.41 (2H, tt, J=7.3 Hz, 7.3 Hz), 1.98-2.10 (6H, m), 2.03 (3H, s), 2.31 (2H, dq, J=1.2 Hz, 6.9 Hz), 2.76 (2H, dd, J=6.5 Hz, 6.5 Hz), 4.06 (2H, t, J=6.9 Hz), 5.28 (1H, dtt, J=10.7 Hz, 6.9 Hz, 1.5 Hz), 5.32-5.41 (4H, m), 5.51 (1H, dtt, J=15.3 Hz, 6.9 Hz, 1.5 Hz); $^{13}$C-NMR (500 MHz, CDCl$_3$): δ=14.25, 20.50, 20.95, 25.49, 26.58, 29.26, 31.91, 32.11, 64.07, 125.34, 127.27, 128.30, 129.65, 131.78, 133.14, 171.08.

Mass spectrum: EI-mass spectrum (70 eV): m/z 250 (M$^+$), 190, 161, 147, 122, 108, 93, 79, 65, 43.

Infrared absorption spectrum (D-ATR): ν=2962, 2931, 1743, 1456, 1364, 1237, 1035, 969, 720.

Column 16, Claim 2, Formula 1: Please remove the formula and replace with the following:
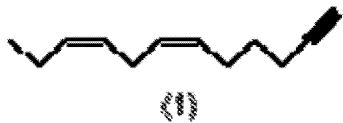
Column 17, Claim 3, Formula 4: Please remove the formula and replace with the following:

The invention claimed is:

1. (6Z,9Z)-6,9-dodecadien-1-yne of the following formula (1):

(1)

2. A process for preparing (6Z,9Z)-6,9-dodecadien-1-yne of the following formula (1):

(1)

the process comprising:
reacting a (3Z,6Z)-10-halo-3,6-decadiene compound of the following general formula (2):

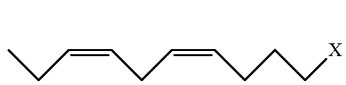

wherein X represents a halogen atom
with a metal acetylide of the following general formula (3):

MC≡CH    (3)

wherein M represents Na, Li, K, Ag, Cu (I), MgZ, CaZ, or Cu(II)Z, wherein Z represents a halogen atom or an ethinyl group
to form (6Z,9Z)-6,9-dodecadien-1-yne (1).

3. A process for preparing (8Z,11Z)-8,11-tetradecadien-3-yn-1-ol of the following formula (4):

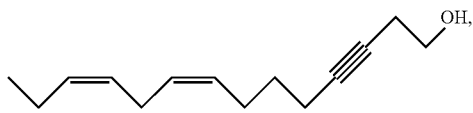

the process comprising:
reacting (6Z,9Z)-6,9-dodecadien-1-yne (1) with a base; and
subjecting a reaction mixture thus obtained to a homologation reaction with ethylene oxide to form (8Z,11Z)-8,11-tetradecadien-3-yn-1-ol (4).

4. A process for preparing (3E,8Z,11Z)-3,8,11-tetradecatrien-1-ol of the following formula (5):

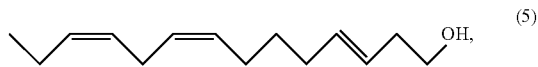

the process comprising:
the process according to claim 3 for preparing (8Z,11Z)-8,11-tetradecadien-3-yn-1-ol (4); and
subjecting (8Z,11Z)-8,11-tetradecadien-3-yn-1-ol (4) to a reduction reaction to form (3E,8Z,11Z)-3,8,11-tetradecatrien-1-ol (5), wherein the reduction reaction is carried out using (i) reduction with an organoaluminum compound, (ii) Birch reduction, (iii) ammonia-free Birch reduction, or (iv) Benkeser reduction.

5. A process for preparing (3E,8Z,11Z)-3,8,11-tetradecatrienyl acetate of the following formula (6):

wherein Ac represents an acetyl group,
the process comprising:
the process according to claim 4 for preparing (3E,8Z,11Z)-3,8,11-tetradecatrien-1-ol (5); and
acetylating (3E,8Z,11Z)-3,8,11-tetradecatrien-1-ol (5) to form (3E,8Z,11Z)-3,8,11-tetradecatrienyl acetate (6).

* * * * *

UNITED STATES PATENT AND TRADEMARK OFFICE
CERTIFICATE OF CORRECTION

PATENT NO. : 11,780,791 B2
APPLICATION NO. : 17/718376
DATED : October 10, 2023
INVENTOR(S) : Miyake et al.

It is certified that error appears in the above-identified patent and that said Letters Patent is hereby corrected as shown below:

On the Title Page

OTHER PUBLICATIONS, Line 1: Please correct "ATTYGALLE et al. "(3E,87,11Z)-3,8,11-Tetradecatrienyl Acetate" to read --ATTYGALLE et al. "(3E,8Z,11Z)-3,8,11-Tetradecatrienyl Acetate--

In the Specification

Column 3, Formula 1, first occurrence: Please remove the formula and replace with the following:

Column 3, Formula 1, second occurrence: Please remove the formula and replace with the following:

In the Claims

Column 16, Claim 1, Formula 1: Please remove the formula and replace with the following:

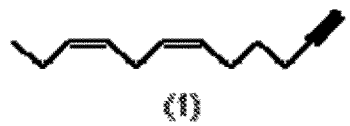

Signed and Sealed this
Twentieth Day of February, 2024

Katherine Kelly Vidal
*Director of the United States Patent and Trademark Office*